United States Patent [19]
McCabe

[11] Patent Number: 5,865,796
[45] Date of Patent: *Feb. 2, 1999

[54] GAS DRIVEN GENE DELIVERY INSTRUMENT

[75] Inventor: Dennis E. McCabe, Middleton, Wis.

[73] Assignee: PowderJect Vaccines, Inc, Madison, Wis.

[*] Notice: The term of this patent shall not extend beyond the expiration date of Pat. No. 5,584,807.

[21] Appl. No.: 767,374

[22] Filed: Dec. 16, 1996

Related U.S. Application Data

[63] Continuation of Ser. No. 376,319, Jan. 20, 1995, Pat. No. 5,584,807, which is a continuation-in-part of Ser. No. 184,812, Jan. 21, 1994, abandoned.

[51] Int. Cl.⁶ .................................................... A61M 5/30
[52] U.S. Cl. .............................. 604/71; 604/24; 239/311
[58] Field of Search ................................ 604/23, 24, 62, 604/68–72, 57–59, 131, 140, 141, 143, 146, 147; 128/200.14, 200.21, 200.22, 200.23; 239/311, 338, 346

[56] References Cited

U.S. PATENT DOCUMENTS

| | | |
|---|---|---|
| 2,632,444 | 3/1953 | Kas . |
| 2,850,013 | 9/1958 | Cordis . |
| 3,744,493 | 7/1973 | Booher et al. . |
| 4,637,816 | 1/1987 | Mann . |
| 4,941,880 | 7/1990 | Burns . |
| 4,945,050 | 7/1990 | Sanford et al. . |
| 5,009,637 | 4/1991 | Newman et al. . |
| 5,015,580 | 5/1991 | Christou et al. . |
| 5,106,370 | 4/1992 | Stewart . |
| 5,120,657 | 6/1992 | McCabe et al. . |
| 5,149,655 | 9/1992 | McCabe et al. . |
| 5,179,022 | 1/1993 | Sanford et al. ........................ 604/69 |
| 5,204,253 | 4/1993 | Sanford et al. . |
| 5,584,807 | 12/1996 | McCabe ................................ 604/71 |

FOREIGN PATENT DOCUMENTS

| | | |
|---|---|---|
| 0 270 356 A2 | 6/1988 | European Pat. Off. . |
| 9007351 | 7/1990 | WIPO .............................. 128/200.22 |
| WO 91/11526 | 8/1991 | WIPO . |
| WO 92/04439 | 3/1992 | WIPO . |
| WO 94/24263 | 10/1994 | WIPO . |

OTHER PUBLICATIONS

Finer et al., "Development of the Particle Inflow Gun for DNA Delivery to Plant Cells," *Plant Cell Reports* 11:323–328 (1992).
Iida et al., "Gene Delivery Into Cultured Plant Cells by DNA–Coated Gold Particles Accelerated by a Pneumatic Particle Gun," *Theor Appl Gent.* 80:813–816 (1990).
Johnston, "Biolistic Transformation: Microbes to Mice," *Nature* 346:776–777 (1990).
Oard et al.; "Transient Gene Expression in Maize, Rice, and Wheat Cells Using an Airgun Apparatus," *Plant Physiol.* 92:334–339 (1990).
Takeuchi et al., "Plant Transformation: A Simple Particle Bombardment Device Basedon Flowing Helium," *Planet Molecular Biology* 18:835–839 (1992).

*Primary Examiner*—Corrine M. McDermott
*Attorney, Agent, or Firm*—Robins & Associates; Thomas P. McCracken

[57] ABSTRACT

A gas driven apparatus for accelerating particles coated with a genetic material into a target comprises a reservoir for releasably retaining a gas at a sufficiently high pressure to detach the particles from the surface of a sample cartridge and to carry the particles through the apparatus toward the target. When leaving the apparatus, the particles entrained in the gas stream pass through a substantially conical exit nozzle which causes the pattern of distribution of the particles to greatly expand. Methods for using the apparatus and for preparing the sample cartridges are also described.

5 Claims, 5 Drawing Sheets

GAS DRIVEN GENE DELIVERY INSTRUMENT

CROSS REFERENCE TO RELATED APPLICATION

This application is a continuation of Ser. No. 08/376,319 filed Jan. 20, 1995, now U.S. Pat. No. 5,584,807, which is a continuation-in-part of Ser. No. 08/184,812 filed Jan. 21, 1994, now abandoned, from which applications priority is claimed pursuant to 35 U.S.C. §120 and which are incorporated herein by reference in their entirety.

FIELD OF THE INVENTION

The present invention relates to the field of delivering material into cells, more particularly to delivering genetic material into living tissue.

BACKGROUND OF THE INVENTION

In the past decade, particle-mediated acceleration of material, particularly genetic material, into living cells and tissues has emerged as an important tool of plant and animal biotechnology. Transient expression and germ line integration of introduced DNA has been demonstrated in microorganisms, plants, and animals.

As the fundamentals of the technology have been worked out, attention has increasingly shifted toward development of devices that offer the operator the ability to perform a series of particle-mediated gene transfers sequentially in rapid succession. Such a device would be particularly advantageous for use in mass immunization of humans or domesticated animals with genetic vaccines.

One limitation of existing particle-mediated gene transfer devices is the form in which the sample is provided. In all such devices, the sample is deposited upon the surface of small, dense particles of a material such as gold or platinum. The coated-particles are themselves then coated onto either a rigid surface, such as a metal plate, or onto a carrier sheet made of a fragile material such as mylar. The coated sheet is then accelerated toward a target. This approach has several advantages as well as some disadvantages. The advantages have to do with the fact that the planar sheet generates a very uniform spread of accelerated particles. One disadvantage is that, each particle-coated plate or carrier sheet is prepared individually and may be used only once, making particle acceleration a time-consuming and inefficient process, particularly when many repetitive gene transfers are envisioned. Each coated carrier sheet is relatively large and must be handled with care, to avoid damage or contamination. It is also sometimes difficult to distinguish the useful coated side of a carrier sheet from the uncoated side. Improper positioning of the carrier sheet can reduce throughput and can result in wasted samples.

The distribution or spread of the pattern of carrier particles may be more critical for some applications, i.e. when germ line events are desired, than for other applications, especially when only transient expression of the introduced genes is needed. When an infrequent germline transformation event is desired, it is necessary to uniformly accelerate particles toward a large area of cells or tissues. To date therefore, it has been considered desirable to distribute the coated-particles as a monolayer on a relatively large surface before accelerating them toward a target to maximize the number of cells receiving particles under precisely uniform conditions, and to thereby increase the likelihood that one cell will undergo a germline transformation. In contrast, when accelerating particles into cells to induce transient gene expression in somatic tissues such as skin, there is a less compelling need to make precisely uniform the acceleration of the particles, since adequate expression can take place even with low numbers of cells actually penetrated by particles. Therefore, particle delivery techniques that to date have been undesirable now become desirable.

To overcome these and other limitations, what is desired is a high throughput gene delivery apparatus that can accept a plurality of samples for rapid and sequential delivery into target tissues. What is also desired is a sample storage and delivery platform that is more durable, and easier to prepare, store, and handle than existing platforms.

SUMMARY OF THE INVENTION

Figure 3:
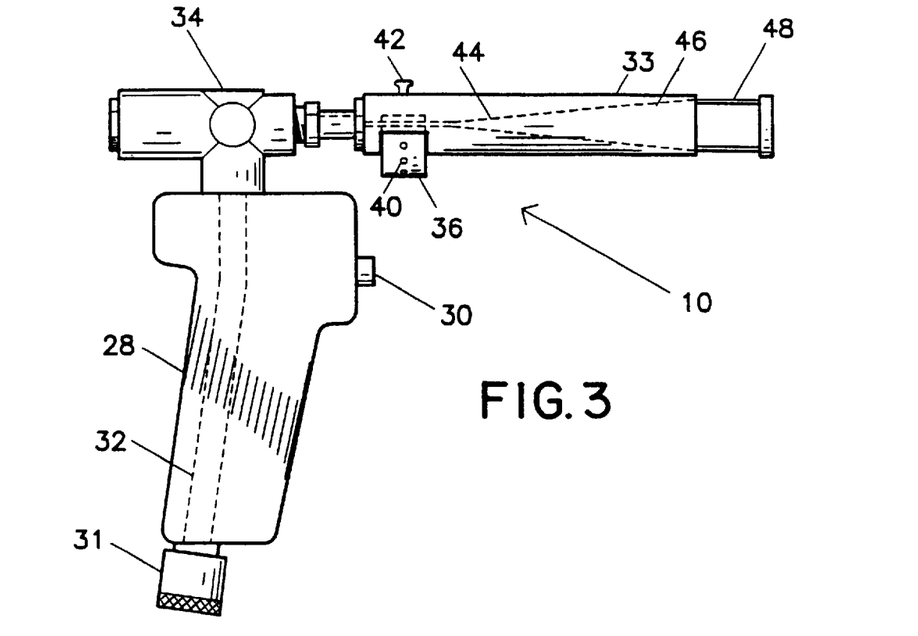
Figure 4:
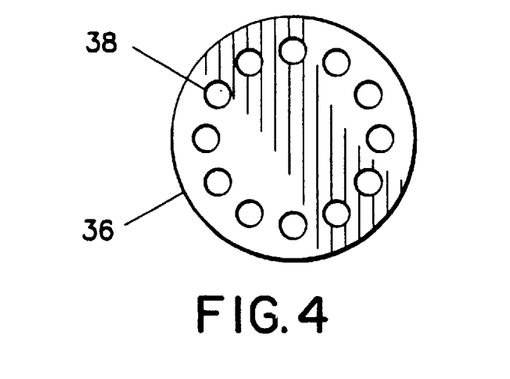
Figure 11:
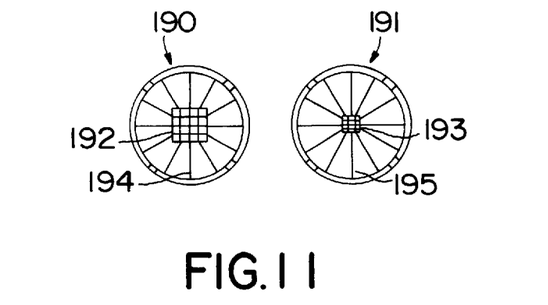

The present invention is summarized in that a gene delivery instrument, designed to be powered by a source of compressed gas includes a body through which an acceleration passage is formed. A valve admits the compressed gas into the acceleration passage. In the body a cartridge chamber is located to receive a particle cartridge with carrier particles coated with biological material. A gas stream admitted by the valve will accelerate down the acceleration passage picking up the carrier particles from the cartridge. At the output end of the acceleration passage from the body a conically tapered exit nozzle tapers so as to expand outward the distribution of the carrier particles as they leave the instrument.

It is an object of the present invention to provide an apparatus for delivering genetic material into tissues or cells in a consistent and repetitive manner.

It is a feature of the present invention that a stored burst of pressurized inert gas dislodges the particles and carries them from the apparatus with sufficient force to enter tissues or cells.

It is an advantage of the present invention that the apparatus accommodates a plurality of samples rather than the single sample accommodated by existing devices.

It is an advantage of the present invention that the samples delivered by the apparatus may be prepared in advance of use and may be stored and handled with ease.

Other objects, features and advantages of the present invention will become apparent from the following specification, read in light of the accompanying drawings.

BRIEF DESCRIPTION OF THE DRAWINGS

FIG. 1 is a schematic depiction of the present invention.

FIG. 2 is a schematic illustration of the effects of varying the angle of the exit nozzle.

FIG. 3 is a side view of a first embodiment of the present invention.

FIG. 4 is a front view of a sample cartridge holder of the embodiment of FIG. 3.

FIG. 5 is a side, cutaway view of a tubular sample cartridge from the embodiment of FIG. 3.

FIG. 6 is a physical map of plasmid pWRG1602.

FIG. 7 is a side view of another embodiment of the present invention.

FIG. 8 is an exploded view of the embodiment of FIG. 7.

FIG. 9 is a cross-sectional view of the valve of the embodiment of FIG. 7.

FIG. 10 is a cross-sectional view of the actuator mechanism of the embodiment of FIG. 7.

FIG. 11 is a plan view of optional diffuser screens for use with the embodiments of FIGS. 3 and 7.

DETAILED DESCRIPTION OF THE PREFERRED EMBODIMENT

Figure 1:
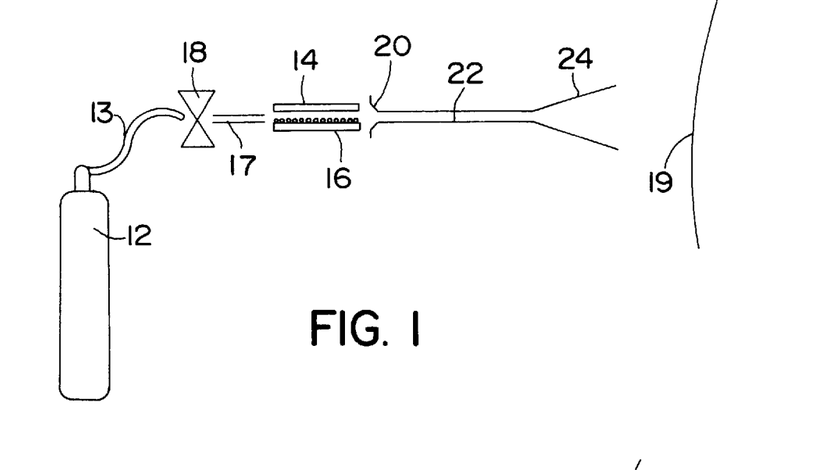

The present invention provides an apparatus and method for rapid and reproducible sequential delivery of particles coated with genetic material into living target tissues and cells. Shown in FIG. 1 is a schematic illustration intended to illustrate the general method of operation of a particle acceleration genetic transformation device operating on the principle of the preferred embodiment here. The parts of the apparatus illustrated in FIG. 1 are shown slightly exploded in some places for purposes of clarity. This illustration is intended to illustrate the basic operating principle of the instrument rather than its construction details.

Referring to FIG. 1, centrally located in the instrument is a carrier particle cartridge 14. The particle cartridge 14 is an elongated concave or tubular structure that has a concave hollow passage down its center. Disposed on the interior of the carrier particle cartridge is a plurality of carrier particles 16. The carrier particles, as will be discussed in further detail below, are small dense particles which have been previously coated with the biological material, i.e. DNA or RNA, intended to be inserted in the target organism. The particles may also be coated with other types of biological materials such as peptides, cytokines, hormones, or protein. A gas valve 18 is located upstream of the carrier particle cartridge and is connected by an appropriate fluid conduit 17 to the interior of the carrier particle cartridge 14. The gas valve is connected, by appropriate tubing indicated at 13, to a source of compressed gas 12. The source of compressed gas 12 can be a conventional commercial compressed gas tank, preferably of an inert compressed gas such as helium. A reservoir of compressed gas is desirable between the gas source 12 and the valve 18, but it has been found that the tubing 13 can function as such a reservoir.

To the right of the carrier particle cartridge is an orifice 20 which gives fluid access to the interior of an acceleration chamber 22 which culminates, in turn, in a conical exit nozzle 24. The patient, tissue, or cells to be treated, designated 19 in FIG. 1, is located at the right hand side of the illustration.

In its general operation, the valve 18 is briefly operated to release a pulse of compressed gas held in the reservoir formed by the tubing 13. Between the valve 18 and the exit nozzle 24, the intermediate parts form a particle acceleration passage through which the expanding gas, previously under pressure, creates a gas stream traveling at significant speed. The gas stream accelerates through the particle acceleration passage and, as it passes through the interior of the particle cartridge 14, the accelerating gas stream picks up the carrier particles 16 and carries them with it. The accelerating gas stream then passes through the chamber 22 to the exit nozzle 24. The particles then pass from the instrument, and on into the tissues of the patient 19 where the carrier particles lodge into, but do not kill, the cells of the target or patient.

Important to the proper functioning of the instrument as illustrated in FIG. 1 is the geometry of the exit nozzle 24. The reason for that importance is illustrated schematically in FIG. 2, which illustrates, as Versions A, B, and C, three different possible geometries of the exit nozzle 24, and their effect upon the flight of the particle 16. In Version A, the exit nozzle 24 does not widen significantly toward the output end of the apparatus. As a result, the exiting gas stream passes linearly out of the end of the exit nozzle 24 and proceeds in a path directly toward the target 19. The carrier particles, as a result, continue in a relatively linear path and all impact a relatively narrow area, designated 25 in FIG. 2, of the patient 19. While the particles 16 diverge somewhat, the divergence is quite small and insignificant.

Figure 2A:
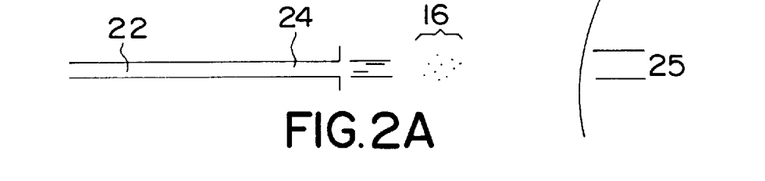
Figure 2B:
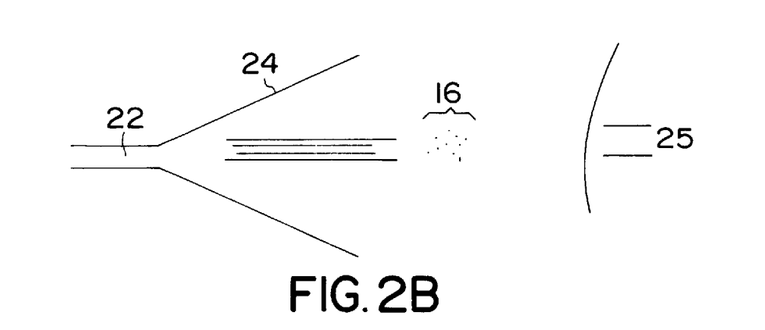

Similarly, in Version B of FIG. 2, the exit nozzle 24 has an exceedingly wide angle of conical taper toward the output end of the apparatus. In this embodiment, as well, the gas stream exits the instrument fairly linearly, and the carrier particles 16 do not disperse widely. Again, the particles impact a relatively compact portion 25 of the patient 19.

Figure 2C:
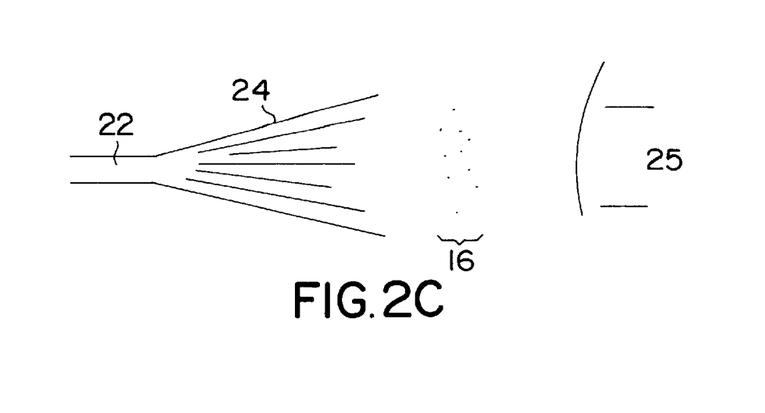

A different phenomenon occurs if, as illustrated in Version C of FIG. 2, the angle of taper of the conical shape of the exit nozzle is less than a critical angle. In this instance, as the accelerated gas stream passes into the exit nozzle, it creates, through a vortex action, a vacuum between the route of passage of the gas stream and the sides of the exit nozzle 24. This vacuum causes the gas stream to be pulled outwardly in all directions perpendicular to the direction of travel of the gas stream. In other words, the dispersion of the gas streams and the particles is lateral to the direction of travel of the particles, which is from the instrument and toward the patient 19. Thus, as is illustrated in Version C of FIG. 2, the gas stream passing out of the instrument is laterally dispersed over a wider area, thereby dispersing the carrier particles 16 carried in it over a wider area, and creating a much more dispersed pattern of carrier particles as illustrated in Version C in FIG. 2. The result is that the particles are distributed over a much wider area 25 of the target organism than would be the case if the conical exit nozzle were not so shaped. Thus the over-dosing of any one small area of the patient with carrier particles is avoided, and a relatively broad and even distribution of the carrier particles is achieved without the need for mechanical distribution of the particles or elaborate gas diverting or distributing equipment.

The exact angle of taper of the conical exit nozzle 24 will vary from embodiment to embodiment depending on gas pressure used and the size of the acceleration chamber 22. For an instrument operated off a commercial helium tank, where the acceleration chamber 22 is $1/16$ inch in diameter, an exit nozzle which tapers from $1/16$ inch to $2/3$ of an inch over a span of 3.3 inches has been found to satisfactorily spread the pattern of particle distribution from about $1/16$ inch to about $2/3$ of an inch in diameter, an increase of over 100 times in the area over which the particles are spread, with a resulting decrease of over 100 times in the density of particle distribution. To work effectively, the conical exit nozzle must be significantly longer in length (e.g. 3.3 inches) than it is in its either initial or final diameters (e.g. $1/16$ to $2/3$ inch). A conical taper which is wider than it is long will not result in a proper dispersion of the particles. It is not necessary that the conical exit nozzle be smoothly conical, however. For example, the exit nozzle can have several small stepped increases in diameter, rather than a continuous increase in diameter, without adversely affecting its overall function.

By varying the pressure of the gas, the force with which particles impact the target 19 and lodge there within may be varied. The gas pressure must be high enough to dislodge the coated particles 16 from the cartridge 14, but not so high as to damage the target 19. When delivering to intact animal skin, a gas stream has been found not to harm the skin. At some gas higher pressures, some minor reddening of the skin occurs at very tolerable levels. The gas pressures in commercially available compressed helium tanks have been found completely satisfactory for detaching the particles 16 and deliver the particles 16 into epidermal cells of a target animal, such as a pig or mouse. Lower pressures or higher pressures may work in certain situations, depending upon the density of the particles, the nature of the target surface and the desired depth of particle penetration. The experience with the pig skin is analogous to that expected with human skin, due to the mechanical similarity of human and porcine skin.

The particle cartridge 14 is preferably concave and is most preferably tubular with particles deposited on its inner surface, since such a cartridge may then be readily handled without touching the carrier particles. While many shapes and geometries of particle cartridge 14 are possible, a simple and functional version is based on using a short segment of tubing of inert material, such as Tefzel®. The tubing forms a cylinder with a cylindrical passage formed through its center. An advantage of this tubular form is that the carrier particles coated with the biological material cannot contaminate the walls of the apparatus. An advantage of the Tefzel® material is that it is transparent, so that loaded cartridges can be visually identified. The identification is by the appearance of the cartridge which will be visibly tinged gold, or have a visible stripe of gold. The inner diameter of the cartridge need only be large enough to allow particles to be deposited therein, and to allow adequate gas flow there through at a pressure sufficiently high to dislodge the particles. The cartridge 14 does not, of necessity, have to be tubular, however, but could be any concave shape in which the pressurized gas is confined, such that the dislodged particles 16 are not dispersed, but rather are directed toward the target by the gas stream. By way of example, the cartridge 14 could be a half tube in which the particles 16 are deposited in the half tube and are covered tightly by a planar or non-planar surface of the apparatus to form a half-cylindrical path through which the gas can pass. Along these lines, the geometries of the sample cartridge and the surrounding chamber formed by a surface of the apparatus are not critical, as long as together the two direct gas flow from the reservoir 12 to the target 19.

Very small carrier particles 16 made of any high density biologically inert material should be acceptable for use as the carrier particles deposited on a surface of the sample cartridge 14. The carrier particles 16 are of dense material so that they will readily retain momentum and are sufficiently small sized so that they are small in relation to the cells of the organism which they are intended to transform. It has been found that carrier particles of a size of a few microns can enter living cells, by penetrating the cell walls thereof, without unduly adversely affecting the ability of most of the living cells to survive. In other words, the carrier particles can enter living cells without killing them, to thus deliver the biological material on the particles into the cell.

Gold is an optimal material for the particles 16 within the present invention since it has high density, is relatively inert to both biological materials and to oxidation, and it readily commercially available in the form of spheres having a diameter of 0.2 to 3 micrometers. Gold spherical particles, or beads, in a size range of 1–3 microns have been successfully used as has gold sold as a microcrystalline powder which has a measured size range of 0.2 to 3 microns.

Tungsten, which has a density of 19, might also be used. Iridium might also be preferable, having a density value of 22, but iridium has not been used by the applicants because it is only easily available in a relatively coarse powder. Tungsten is also probably less desirable compared to gold because it tends to oxidize in air and in the presence of even trace moisture. Such an oxidation layer on the carrier particles tends to bind the particles together causing severe increase in average particle size as the particles aggregate together. Particles which are clumped in irregular aggregations are less desirable for the practice of the present invention since such aggregations will vary widely in their mass and size, thus leading to difficulty in obtaining regularly replicable results.

Illustrated in FIG. 3 is a side view of an embodiment of a particle acceleration apparatus 10 constructed in accord with the present invention. The device shown is hand-manipulable and portable, so that it may be readily and easily handled and moved by the experimenter, technician or clinician.

Turning to the details of the apparatus of FIG. 3, the device includes a handle 28 that is preferably elongated and can be of any suitable shape or size adapted to the needs and comfort of the particular user of the apparatus. As shown in the FIG. 3, the handle 28 is formed into the shape of a pistol grip to provide the operator with a firm grip and ready access to a valve trigger mechanism 30.

Passing through the handle 28 is an inlet tube 32, open at both ends and formed of a solid material that can contain gas at the pressures used by the device. Thus, it is preferred that the inlet tube 32, and all other portions of the apparatus (other than the sample cartridge) that contact the pressurized gas stream be formed of a non-deformable solid material, such a metal, preferably brass, or a high density thermoplastic or resin material. The inlet tube 32 acts as a reservoir, described above, providing releasable storage for enough gas at operating pressure to accomplish one particle-accelerated delivery. The dimensions of the inlet tube 32 are not critical, and may be increased or decreased to accommodate sufficient gas under pressure. A separate dedicated gas reservoir may be provided, if the volume within the inlet tube 32 is insufficient.

To one end of the inlet tube 32 is a connector 31 that is connectable to the external gas source 12. The gas source can be a commercial tank of a biologically and chemically inert compressed gas. The inert gas is preferably helium. The pressure at which gas leaves the gas source is advantageously regulated by a conventional pressure regulator valve and displayed on a gauge visible to the operator.

Connected at the opposite end of the inlet tube 32 is a valve 34, that controls flow of the gas from the inlet tube 32 to the elongated body 33 of the apparatus 10. In the first embodiment of FIG. 3, the valve 34 is an electrically-actuated solenoid piston valve operated by a valve trigger mechanism 30 on the handle 28. Advantageously, the wires between the valve 34 and the trigger mechanism 30 are buried within the handle 28 to improve the safety and manageability of the apparatus in use. The invention is not limited to the particular type of valve shown or to any particular actuator or trigger mechanism. Many valve and trigger combinations are known that may be substituted by one of ordinary skill for the combination shown herein, as exemplified by the second embodiment described below. Many combinations of valve and actuator are suitable, as long as the valve piston and valve body can withstand the pressure of the gas stream entering from the inlet tube 32.

The fluid outlet of the valve 34 is in fluid connection with a cartridge holder 36. In a preferred embodiment, that facilitates rapid sample reloading, a multi-cartridge holder 36 is provided. To maximize the number of samples that may be preloaded in a single step before operating the device, the multi-cartridge holder is cylindrical. A front view of the cylindrical cartridge holder 36 is shown in FIG. 4. A plurality of cartridge chambers 38, each sized to receive one particle cartridge 14, are arranged in a circular manner at a fixed distance along the radii of the cylindrical holder so that one cartridge chamber 38 may be positioned in the gas stream during each delivery. The holder 36 rotates 360° about its radial axis. A plurality of detents 40 on the periphery of the cartridge holder 36 engage a nub to identify each position in which a chamber 38 is within the path of the gas. The nub may be provided by providing a spring biased projection 42 through the body 33 to engage the nub on the cartridge holder. The cartridge holder 36 could assume other shapes, holding more or fewer samples depending upon the needs of the user. The cartridge holder 36 need not be cylindrical as shown, but could be a linear arrangement of sample cartridges that may be moved into position to receive the gas stream that passes through the valve 34.

A hollow particle acceleration chamber 44 in the body 33 provides a path toward the target for the gas stream carrying particles. The chamber 44 has been constructed with a diameter of 1/16 of an inch, and is 12 to 15 mm in length. If the chamber 44 is too long, the gas stream slows due to friction. As is revealed in the cutaway portion of FIG. 3, the diameter of the hollow chamber 44 increases at its distal end to form an exit nozzle 46 that allows adequate dispersion of coated particles entrained in the gas flow. Attached to the distal end of the particle acceleration chamber 44, beyond the exit nozzle 46, is a spacer 48 that allows the operator to set a fixed distance between the apparatus 10 and the target. The proper distance may be determined and fixed as needed, on the basis of empirical observations of the appearance target cells and extent of gene expression after delivery. It has been found for mammalian skin that a spacer of 3/4 to 1 inch works well. It has been found that polishing the interior of the chamber 44 has a beneficial effect on the operation of the device 10. This may be done by coating a string or pipe cleaner with a polishing compound and using it to polish the interior of the chamber 44. This reduces drag and interaction with the sides of the chamber 44 and thus facilitates the carrier particles flowing on toward the intended target. The exit nozzle 46 may be similarly polished. It has been found advantageous to restrict the area through which the gas flows after the valve 34, before reaching the start of the chamber 44 by filling the space with an appropriate spacer, as illustrated in more detail with regard to the embodiment of FIG. 7 below.

Figure 5:
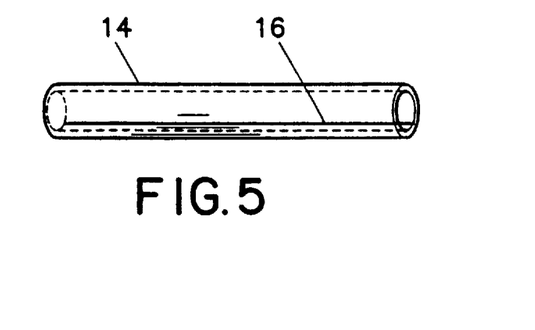
Figure 6:
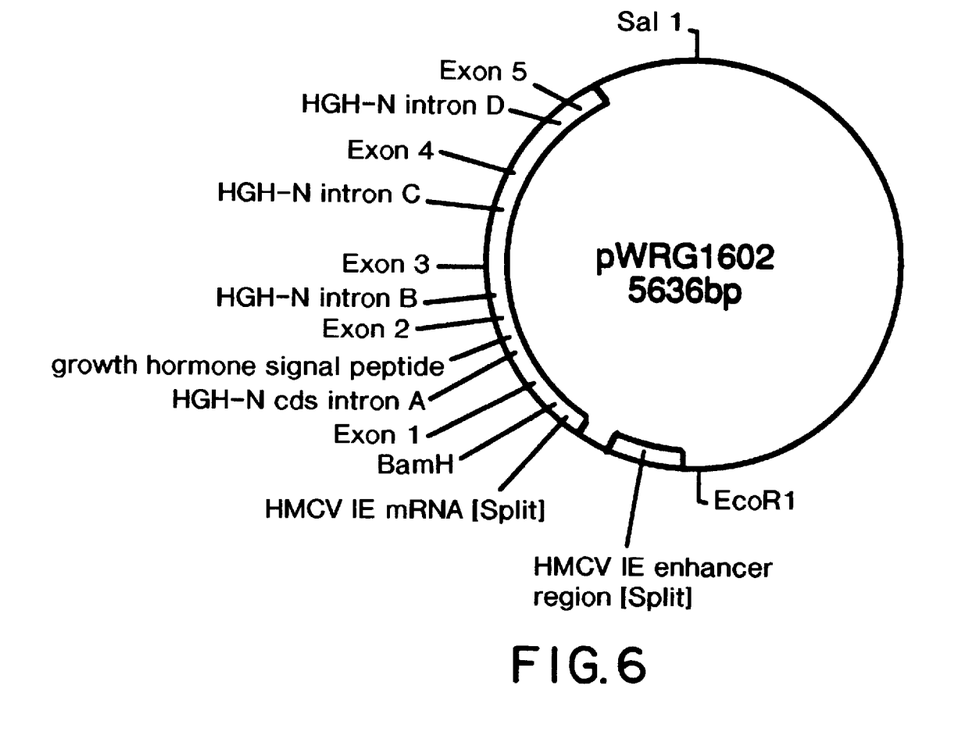

A large number of a useful sample cartridges 14, shown in FIG. 5, bearing coated particles 16 may be prepared in a single procedure as follows in a number of different methods. Two differing methods have been successfully used.

Under the first method, a suspension of biological materials coated particles, prepared in a manner known to the art, is introduced into a length of plastic tubing and the particles allowed to settle under the force of gravity to the bottom of the tubing inner surface. When the particles have settled, forming a ribbon of particles along the full length of the tubing, the liquid is drained from the tubing and the tubing is rotated to spread the beads over the inner surface as they are dried under nitrogen. The tubing is then cut into lengths appropriate for the insertion into the sample chambers of the delivery apparatus. One of ordinary skill will recognize that the number of coated particles available for transfer may be varied by adjusting the concentration of the particle suspension, or by adjusting the length of tubing used to form a cartridge. One will also recognize that sample cartridges useful in the present invention may be prepared in ways other than that just described. One of ordinary skill is familiar with other ways to detachably secure sample-coated particles to a surface.

A second method uses a slight adhesive effect to secure the carrier particles 16 in the particle cartridge 14. It has been found that such a slight adhesive helps to ensure that the particles are accelerated well by keeping them adhered temporarily to the interior concave surface of the cartridge until the gas stream rises to full pressure. To accomplish this, an additive is used when the particles are suspended in alcohol. Additives which are only slightly adhesive and which have been used with success are polyvinyl pyrrolidone (PVP), cholesterol, glycerin and water. Cholesterol, for example, is used at a rate of 1 mg cholesterol per ml of alcohol in the suspension. The particle/alcohol suspension is sonicated, to help the suspension, then the suspension is merely placed inside the cartridge 14 which is placed on its side. The carrier particles rapidly fall out of suspension along one side of the interior surface of the cartridge. The alcohol can then be removed and the interior of the cartridge dried with a nitrogen stream as the tube is rotated.

Figure 7:
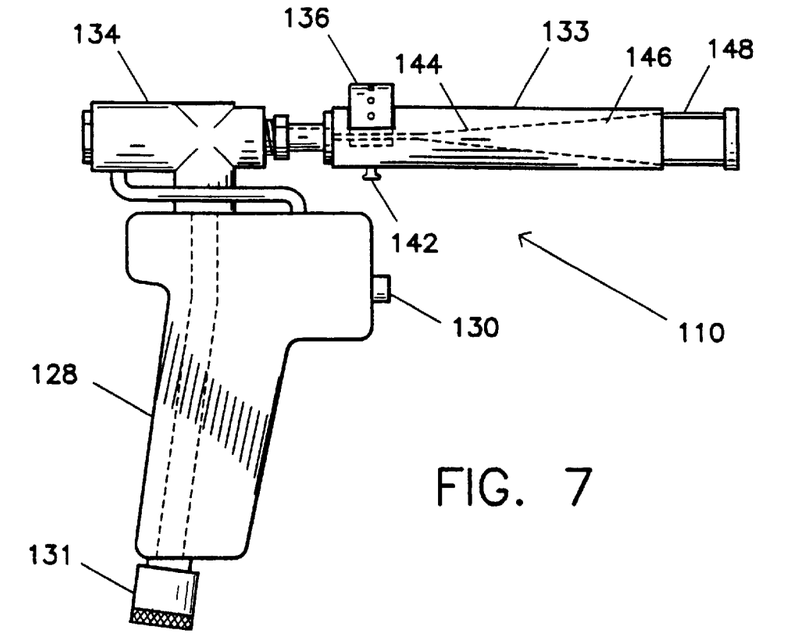
Figure 8:
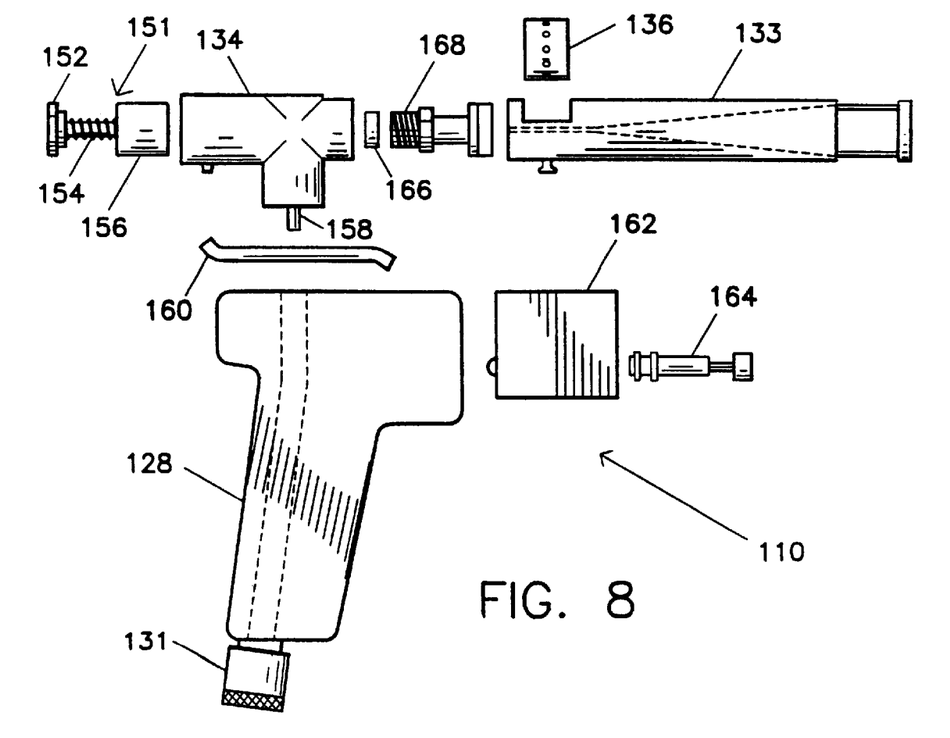

Shown in FIGS. 7 and 8 is another embodiment of a particle acceleration device constructed in accordance with the present invention. In the device 110 of FIGS. 7 and 8, elements which have similar or corresponding function to those in the embodiment of FIG. 3 have been assigned similar reference numerals incremented by 100. For example, the handle 128 and trigger 130 of the embodiment of FIG. 7 appear like the handle 28 and the trigger 30 of the embodiment of FIG. 3. In the device 110 of FIG. 7, the valve 134 for releasing the gas pulse operated by a fluid actuation system adapted from the solenoid used in the embodiment described above. The valve 134 is connected to the trigger 130 by a fluid conduit 160.

In the exploded view of FIG. 8 additional internal components of the device of FIG. 7 are visible. A valve member 151 screws into the end of the housing of the valve 134. The valve member includes a threaded fitting 152 from which extends a spring-loaded biasing shaft 154 on the end of which is mounted a valve member 156. A capillary or helium bleed tube 158 which has an opening of about 50 microns, extends across the valve 134 to provided a continuous low-level bleed of helium gas through the device 110. A tube 160 connects the left-hand side of the valve 134 with an actuator block 162. A trigger/plunger 164 is received inside the actuator block 162. A spacer 166 and a fitting 168 serve to connect the valve 134 with the cylindrical body 133. The spacer has an internal passage through it of about 1/4 inch to limit the volume into which the gas flows after the valve 134. At the point at which the gas passageway enters the body 133, an entrance point of about 0.11 inches is provided so that the expanding gas will be accelerating as it passes through the cartridge holder 136. The body 133 and the cartridge holder 133 are otherwise similar to those of the embodiment of FIG. 3 except that the cartridge holder 136 is located on the top side of the body 133 rather than the bottom side.

Figure 9:
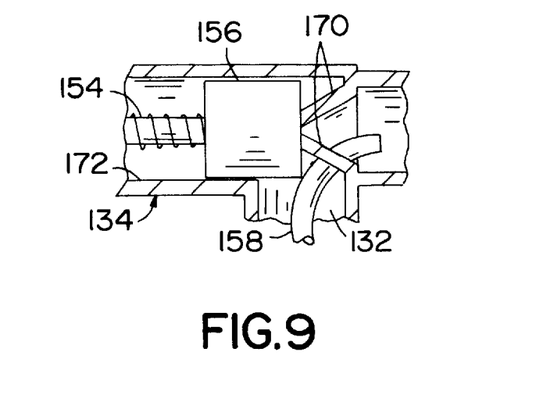

The details of the valve 134 are shown in FIG. 9. An inlet gas tube 132, similar to the inlet gas tube 32 of the first embodiment, connects to the base of the valve and provides input pressurized gas. The valve member 156 rests, when the valve 134 is in its normally closed state, resting against a conically tapered valve seat indicated at 170. The bore of the interior of the valve 134 is a cylinder 172 which fits close to, but is not in fluid-tight contact with, the valve member 156. As viewed in FIG. 9, the chamber to the left of valve member 156 is where the tube 160 connects to the valve 134.

Figure 10:
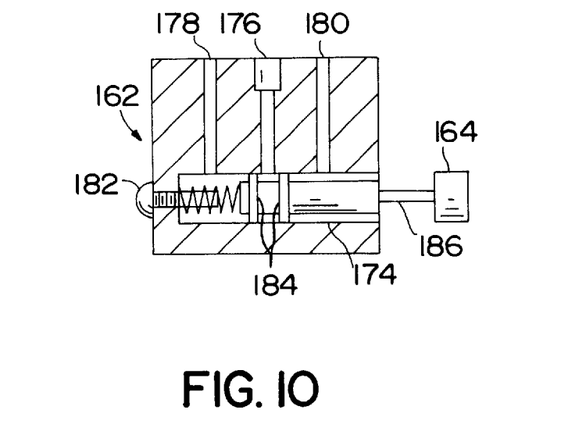

Shown in FIG. 10 are further details of the actuator 162. Extending horizontally into the actuator block 162 is a shaft 174, which opens only to the front of the actuator block 162.

Three vertical bores 176, 178 and 180 are formed extending downwardly from the top of the actuator block and in fluid communication with the shaft 174. The top of the bore 176 is sized to receive the other end of the tube 160 while the shafts 178 and 180 are small and simply open to the ambient atmosphere. A restraining pin 182 extends into the closed end of the shaft 174 to limit the movement of the trigger plunder 164, and the restraining pin includes a spring to bias the plunger to rest in its position as shown in FIG. 10. The plunger 164 is an elongated shaft with two O-rings positioned on it which seal against the interior of the shaft 174. A shaft extension 186 connects the actual trigger button at the end of the plunger 164 to the elongated shaft inside the shaft 174.

In the operation of the device 110, the inlet 131 is connected to the supply of high-pressure gas, preferably helium. The capillary tube 158 provides a small low level leakage or bleed of helium across the valve 134 and into the interior of the body 133, to flood helium into the exit nozzle 146. This is done so that helium is the predominate gas in the exit nozzle 146 and between the exit nozzle and the target even before the device is operated. Helium in this area provides a lower drag on the flow of the carrier particles and more consistent operation of the device 110.

The valve member 156 normally sits against the valve seat 170 as shown in FIG. 9. The entire interior of the valve 134 is connected by the tube 160 with the vertical bore 176 in the actuator block 162. As long as the plunger 164 is at its position shown in FIG. 10, the lower end of the bore 176 is sealed by the O-rings 184 and no gas is lost by this route. When the trigger/plunger 164 is depressed by the user, against the force of the spring on the restraining pin 182, the O-rings pass to the left of the base of the bore 176. This permits the gas in the bore 176 to vent to the atmosphere through the bore 180. This venting has the effect of lowering the pressure on the left-hand side of the valve member 156. The walls of the chamber 172 prevent unrestricted fluid flow to the left-hand side of the valve 134 and hence the pressure on the right-hand side of the valve member 156 is greater that on the left-hand side. The spring 154 is chosen so that this pressure differential is sufficient to cause the valve member 156 to be forced to the left as viewed in FIG. 9, and the valve member 156 separates from the valve seat 170, opening the flow of high pressure gas through the cartridge and into the body 133. This condition persists until the trigger is released, after which the trigger/plunger 164 is returned to its position shown in FIG. 10, sealing the bottom of bore 176. This allows high pressure to return to the left-hand side of the valve 134, and the valve member 156 returns to seat against the valve seat 170 to close the flow of gas through the valve 134.

After the valve 134, the device maintains a relatively constant area for gas flow unit until the restriction prior to entering the cartridge carrier. The spacer 166 is intended to fill the space left between the fitting 168 and the valve seat 170, except for a central bore through the spacer 166 approximately equal in diameter to the diameter of the bore through the body 133. The concept is to restrict the area for the gas to expand to a ¼" bore until it reaches the 0.11" inlet port for the cartridge holder.

There is some evidence to indicate that a diffuser placed at the output end of the device 110, at it right-hand end as viewed in FIG. 7, will help the efficiency of gene delivery. Two such diffusers are shown in FIG. 11, indicated at 190 and 191. Each diffuser includes an annular ring and a centrally positioned screen 192 and 193 respectively suspended in place by wires 194 and 195. The diffuser acts to selectively remove part of the beads from the center of the pattern to result in a more even distribution of carrier particles in the target area.

The apparatus described herein is advantageously used for mass vaccination of humans or domestic animals using a genetic vaccine. Genetic vaccines are formed of genetic material, usually DNA, that is derived from a pathogenic agent and that is then delivered into living cells of an organism using a device like that shown here. Once in a cell, the genetic material is expressed by the cellular transcription and translation machinery to produce a protein or peptide which engenders an immune response in the organism, the immune response making the animal or person resistant to subsequent infection by the agent from which the genetic material originated. This apparatus may also be used for gene therapy whereby genes are delivered which are lacking in, but needed by, the organism. Alternatively, it may be possible to stably integrate such genetic material within the genetic material of a genetically deficient organism, and in so doing, correct the genetic deficiency, at least in certain somatic cells.

While the apparatus thus described was designed for its utility in large scale, repetitive deliveries of genetic vaccines, it can also be used in the same ways that existing particle acceleration devices have been used in single delivery methods, including, but not limited to, transfer of genetic material into the organs, tissues, and cultured cells of plants and animals. The device has been successfully used to deliver genes into the meristems of living plants to create transgenic plants. All of the advantages of this apparatus, particularly its portability and easy sample handling, apply equally well when the apparatus is used for one-shot delivery of a gene by particle acceleration. However, the principle of the invention may also be incorporated into a stationary non-portable unit to achieve substantial advantages in speed, reproducibility and ease of use.

EXAMPLE

1. Plasmid

In plasmid pWRG1602, illustrated by the plasmid map of the FIG. 5, the hCMV immediate early promoter directs expression of a human growth hormone (hGH) gene. The hGH coating sequence is contained within an XbaI-EcoRI fragment of approximately 2.2 kbp, which was itself obtained from plasmid pGH (available from Nichols Institute). The hCMV immediate early promoter, described in 5 EMBO J. 1367–1371 (1986), is contained within a 619 base pair AccII fragment which encompasses the region from 522 base pairs upstream to 96 base pairs downstream of the CMV immediate early transcription initiation site. Plasmid DNA was prepared using standard molecular biology techniques.

2. Preparation of DNA coated particles

Copies of the pWRG1602 plasmid were then coated onto gold carrier particles. This was done by mixing 26 mg of precipitated gold powder (0.95 micron average diameter) with 200 μl of 0.1M spermidine in 25 μg of DNA. The ratio of DNA to gold was 2.5 μg of DNA per mg of gold. Then, 200 μl of a 2.5M calcium chloride solution was added to the mixture, while continuously agitating, after which the sample was incubated an additional 10 minutes at room temperature to permit precipitation of the DNA onto the carrier particles. The mixture was centrifuged for 3 seconds in a microcentrifuge to concentrate the carrier particles with the DNA thereon, after which the carrier particles were washed gently with ethanol and resuspended in 3 ml of ethanol in a capped vial. The resuspension of the carrier particles in the ethanol was aided by the immersion of the vial in a sonicating water bath for several seconds.

3. Delivery of coated particles into animal tissue.

Anesthetized mice were clipped closely to remove most of the fur from the target site. The transformations were conducted on this denuded site on the animal.

Sample cartridges thus prepared were loaded into the apparatus of the present invention for laboratory testing. In a first test, the compressed gas was delivered at various pressures to determine the effect of gas pressure upon gene delivery. To assay the effectiveness of the procedures, twenty-four hours after treatment, the target skin was removed and homogenized. The level of human growth hormone (hGH) in each sample was quantitated using a commercial ELISA-based assay for hGH. Table 1 demonstrates the approximate amount of human growth hormone (hGH) produced by the transformed cells in the mouse epidermis per delivery site.

TABLE 1

| Mouse | Pressure | Delivery Site | Amount |
|-------|----------|---------------|--------|
| A     | 500 psi  | 1             | 40 ng  |
|       |          | 2             | 22 ng  |
|       | 700 psi  | 1             | 59 ng  |
|       |          | 2             | 140 ng |
| B     | 500 psi  | 1             | 40 ng  |
|       |          | 2             | 38 ng  |
|       | 300 psi  | 1             | 75 ng  |
|       |          | 2             | 50 ng  |

In an experiment designed to measure hGH protein expression, another pWRG1602 sample cartridge prepared as described was loaded into the apparatus and the particles coated thereon were delivered in vivo into a surgically exposed mouse liver at 500 psi. When the liver and serum were examined twenty-four hours post-delivery, both showed low levels of hGH, three and two fold above background levels, respectively.

A set of sample cartridges containing a total of approximately 0.5 milligrams of gold and DNA per cartridge were prepared. These cartridges were loaded into the apparatus and particles were delivered at a variety of pressures into the epidermis of an anesthetized pig. No pretreatment of the skin was performed prior to particle delivery. Twenty-four hours after treatment, the skin patches treated were removed and assayed for hGH using the ELISA assay. At 650 psi, several sites showed erythema at the delivery sites. At the one site that showed the least erythema, 937 ng of hGH was detected. At 800 psi, most sites showed erythema; 412 ng of hGH was detected in the site showing the least erythema. At 1100 psi, no hGH was detected at any delivery site and all exhibited significant erythema at this delivery pressure.

I claim:

1. A gene delivery instrument comprising:
    a body having a particle acceleration passage formed therein, said acceleration passage having an opening at one end thereof;
    means for connecting the acceleration passage with a source of compressed gas to selectively admit gas into said passage, thereby forming an accelerating gas stream;
    a cartridge chamber adapted to accept and retain a particle cartridge containing carrier particles coated with a genetic material, said cartridge chamber arranged within the acceleration passage such that the accelerating gas stream passing through the acceleration passage picks up and accelerates carrier particles from the cartridge; and
    an exit nozzle at the opening of the acceleration passage, said exit nozzle widening substantially away from the body wherein the widening portion of the nozzle is longer than it is wide.

2. The instrument of claim 1, wherein the means for connecting the acceleration passage with a source of compressed gas comprises a valve which controls the flow of gas from the source to the acceleration passage.

3. A gene delivery instrument comprising:
    a body having a particle acceleration passage formed therein, said acceleration passage having an opening at one end thereof;
    means for connecting the acceleration passage with a source of compressed gas to selectively admit gas into said passage, thereby forming an accelerating gas stream;
    a cylindrical cartridge chamber adapted to accept and retain a tubular particle cartridge which contains on the interior surface thereof carrier particles coated with a genetic material, said cartridge chamber arranged within the body and communicating with the acceleration passage such that the accelerating gas stream passes through the particle cartridge to pick up and accelerate carrier particles from the cartridge; and
    an exit nozzle at the opening of the acceleration passage, said exit nozzle widening substantially away from the body wherein the widening portion of the nozzle is longer than it is wide.

4. The instrument of claim 3, wherein the means for connecting the acceleration passage with a source of compressed gas comprises a valve which controls the flow of gas from the source to the acceleration passage.

5. A particle cartridge for use in a compressed gas-driven gene delivery instrument, said cartridge comprising a concave body having an arcuate passage formed on a surface thereof wherein said arcuate passage contains a deposit of carrier particles coated with genetic material.

* * * * *